United States Patent [19]
Pijanowski et al.

[11] Patent Number: 5,449,069
[45] Date of Patent: Sep. 12, 1995

[54] SURGICAL INSTRUMENT PROCESSING AND DELIVERY DEVICE

[75] Inventors: Martin Pijanowski, Holiday, Fla.; John C. O'Brien, Annandale, N.J.

[73] Assignee: Nitro-Wear Technology, Inc., Annandale, N.J.

[21] Appl. No.: 176,739

[22] Filed: Jan. 3, 1994

[51] Int. Cl.⁶ .......................... B65D 83/10; A47F 7/00
[52] U.S. Cl. ...................... 206/370; 206/372; 206/493; 211/70.6; 422/300; 422/310
[58] Field of Search .............. 206/370, 372, 375, 363, 206/493, 438; 211/70.6, 88; 422/300, 310, 297

[56] References Cited

U.S. PATENT DOCUMENTS

| | | | |
|---|---|---|---|
| 2,903,129 | 9/1959 | Anderson, III | 206/363 |
| 3,925,014 | 12/1975 | Langdon . | |
| 4,135,868 | 1/1979 | Schainholz | 422/310 |
| 4,229,420 | 10/1980 | Smith et al. . | |
| 4,342,391 | 8/1982 | Schainholz . | |
| 4,448,750 | 5/1984 | Fuesting | 422/300 X |
| 4,512,466 | 4/1985 | Delang | 206/370 |
| 4,577,755 | 3/1986 | Ramsay . | |
| 4,643,303 | 2/1987 | Arp et al. | 206/370 |
| 4,865,821 | 9/1989 | Langdon . | |
| 4,911,297 | 3/1990 | Suburu | 211/70.6 X |
| 5,137,151 | 8/1992 | Choate . | |
| 5,215,726 | 6/1993 | Kudla et al. . | |

Primary Examiner—Bryon P. Gehman
Attorney, Agent, or Firm—Kenyon & Kenyon

[57] ABSTRACT

A surgical instrument rack is provided for improving the efficiency, quality, and safety of the processing and delivery of ring-handled surgical instruments. The rack includes a base having opposing front and rear panels, each having multiple slots therein for supporting the instruments. Each slot in the front panel corresponds to one of the slots in the rear panel so that the end of each of the surgical instruments having the ring handles can be positioned in the slot in the front panel and the opposite end of the instrument can be positioned in the corresponding slot in the rear panel. The instruments can thus be held in an upstanding, parallel, side-by-side arrangement. The base also includes apertures therein near the front panel for receiving a spindle such that the spindle may be extended through the apertures and the first ring handles of the surgical instruments to couple the instruments with the base. The rack also includes a rack top having apertures therein for receivng another spindle so that the spindle can be extended through the apertures and the other ring handles of the surgical instruments. The rack top is pivotally connected with the base near the rear panel so that the surgical instruments can be moved between open and closed positions by pivoting the rack top relative to the base.

43 Claims, 6 Drawing Sheets

SURGICAL INSTRUMENT PROCESSING AND DELIVERY DEVICE

FIELD OF THE INVENTION

The present invention relates to racks or devices for the processing and delivery of ring handled surgical instruments. More specifically, the invention relates to devices addressing OSHA safety standards for the handling and cleaning of instruments (Federal Register, Vol. 56, No. 235, Page 64178).

BACKGROUND OF THE INVENTION

Surgical procedures today generally require the use of multiple instruments like clamps, forceps, and retractors. Over the years, surgical procedures along with the type and quantity of instruments used in a given procedure have become substantially standardized. Many of the above-mentioned instruments are scissor type instruments, having a pair lever members that are connected through a pivot to working members. The lever members typically include ring handles at the ends thereof to facilitate the opening and closing of the instrument by a user's fingers.

Instruments used in surgical procedures are typically processed as follows. Dirty or used instruments received from the operating room are removed from a container in which the instruments have been carried and placed loosely in a sink typically filled with water and a cleaning solution. After the instruments have been soaked, they are removed by hand, individually cleaned with a brush, and rinsed. The instruments are then inspected, counted, and organized in the order of use. They are then placed on "stringers", which are oval shaped metal rods inserted through the handles of the instruments. The open ends of the stringers are closed with clamps to prevent instruments from being accidently removed. The strung instruments are then placed into one of a variety of commercially available sterilization baskets or containers. The container and instruments therein are sterilized with steam or ethylene oxide and then presented to operating room staff for their intended use.

The operating room circulating nurse will open the container for presentation of the instruments in a sterile field. The scrub nurse will remove the instruments, which are still attached to the stringers, from the container and place them on an instrument roll. (The instrument roll is typically made from a sterilized towel that the scrub nurse has formed into a roll.) The stringers are then removed and the instruments are counted. Once the surgical procedure is completed, the instruments are again counted. They are then placed in a basin or back in the container with any gross contamination removed and returned to the central supply.

Much time is wasted during the cleaning, organizing and counting procedure in the central supply. In addition, the onset of AIDS and other infectious diseases has dramatically increased the biohazard risk for central supply personnel. In response, OSHA has established the previously cited new standards for the handling of surgical instruments, particularly sharps.

The typical procedure for setting up the operating room, including removing the stringer, creating an instrument roll, and counting the instruments, is also time consuming. Counting the instruments before and after the surgical procedure is particularly important for ensuring that no instruments are left in the patient after the procedure has been completed. Designated operating room personnel have the responsibility to maintain a count of the instruments, and their mental alertness and memory must be relied upon to prevent mistakes. Also, post operative x-rays of patients, which have become generally routine, may give the operating room staff a false sense of security.

Clamps and other instruments are often lost with the patient draping. The instruments maybe difficult to recover especially if they are disposed in a "red bag" and incinerated. Hospital procedures restrict employees from opening these bags once closed and removed from the operating room.

A variety of devices exist for storing and handling surgical instruments. For example, U.S. Pat. No. 3,925,014 issued for Langdon discloses a wire rack type device for storing and supporting surgical instruments. This device employs special clamps to hold and group instruments and does not lend itself to easy use in an autoclave. The working members of the instruments are generally limited in the degree to which they can be opened, and the instruments may have to be removed to ensure complete cleaning. Also, no mechanism is provided for preventing the working members coming into contact with each other. Furthermore, the retaining bars of the device, which engage the instruments, may scratch or damage the instruments.

Other instrument racks are disclosed in U.S. Pat. Nos. 4,342,391 issued to Schainholz, 4,229,420 issued to Smith et. al., 4,577,755 issued to Ramsay, and 5,137,151 issued to Choate. These racks share many of the same problems as the Langdon device. For example, the working members of instruments stored in the Schainholz, Smith et. al. and Choate devices are not prevented from coming into contact with each other. Moreover, the devices disclosed in these patents include wound wire rings or boots, which make the cleaning process difficult and may necessitate the removal of the instruments from the rack for complete cleaning. Additionally, the Choate design does not provide adequate drainage to facilitate removal of gross contaminants. With the possible exception of the Smith, et. al. patent, the references disclose devices made of metal parts that engage the instruments, thereby increasing the likelihood of scratching or otherwise damaging the instruments, which are often delicate and expensive.

SUMMARY OF THE INVENTION

A surgical instrument rack is provided for improving the efficiency, quality, and safety of the processing and delivery of ring-handled surgical instruments. The rack includes a base having opposing front and rear panels, each having multiple slots therein for supporting the instruments. Each slot in the front panel corresponds to one of the slots in the rear panel so that the end of each of the surgical instruments having the ring handles can be positioned in the slot in the front panel and the opposite end of the instrument can be positioned in the corresponding slot in the rear panel. The instruments can thus be held in an upstanding, parallel, side-by-side arrangement. The instruments are thus prevented from coming into contact with each other, thereby reducing damage and enabling easier handling of the instruments. The base also includes apertures therein near the front panel for receiving a spindle such that the spindle may be extended through the apertures and one of the ring handles of the surgical instruments to couple the instruments with the base. The rack also includes a rack top having apertures therein for receiving another spindle, which can be extended through the apertures and the other ring handles of the surgical instruments. The rack top is pivotally connected with the base near the rear panel so that the surgical instruments can be moved between open and closed positions by pivoting the rack top relative to the base.

The sides of the base include a three position cam like mechanism, which allows the rack top to be oriented at 0°, 15° and 30° angles relative to the base and the instruments to be correspondingly moved between closed and widely opened positions to facilitate cleaning, sterilization and use of the instruments. The 30° opening allows the instruments to be cleaned without their removal from the device. The device enables the position of the instruments to be changed without applying excessive force to or causing misalignment of the instruments.

Removable tabs may be positioned in slots not occupied by instruments to allow a user to quickly and easily confirm the count of the instruments.

A customized brush may be provided for cleaning instruments in the device without their removal from the device.

The bottom of the base includes strategically-located multiple drainage ports to prevent gross contaminants from being trapped in the device during the cleaning process.

Tabs and corresponding apertures are provided in the base to enable multiple devices to be stacked onto one another for storage.

For presentation of the surgical instruments in the operating room, the spindles and rack top are first removed from the device. The instruments are presented with the lever members oriented at an upward angle in the base of the device, which alleviates the need for an instrument roll. Once used, the instruments are returned to the base. The rack top and spindles are then reattached to the base. The instruments can then be efficiently cleaned and counted without their removal from the device.

The entire device comprises injection molded parts that are made from a generally rigid, autoclavable and ethylene oxide sterilizable polymeric material. This type of material is preferable over metals because it is relatively light weight, can have a light color (e.g., white), and affords greater protection against possible scratching or other damage to the instruments caused by metal members and retainers engaging the instruments. The single unit construction of the base with its multiple drainage ports prevents the accumulation of foreign matter like tissue and blood, minimizes premature product failure, and eliminates rust or corrosion of the welded joints as may occur with metal devices.

Instrument racks in accordance with the invention may be used with general surgical instruments as well as other instruments like dental and veterinary instruments.

DETAILED DESCRIPTION

Figure 1:
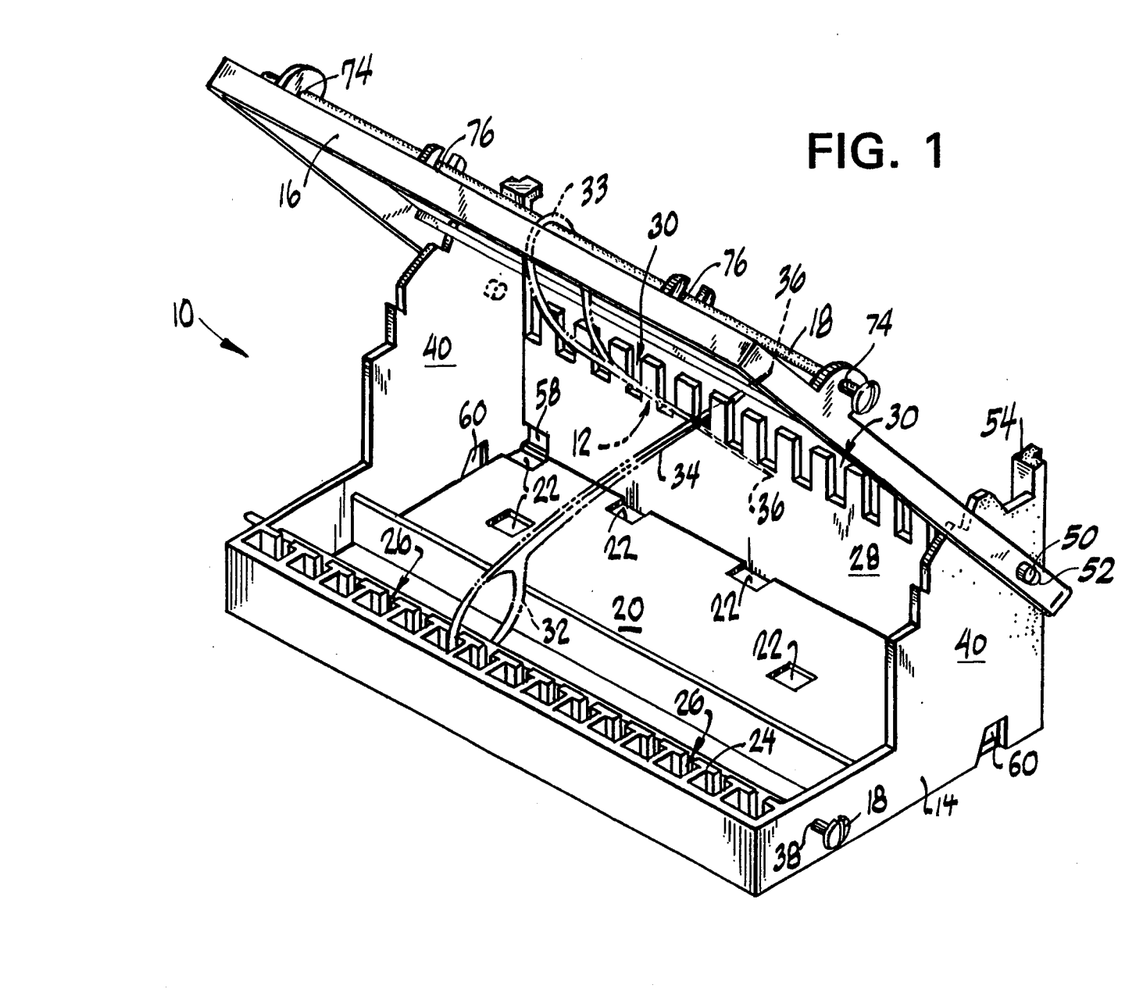
FIG. 1 is a perspective view of an instrument processing and delivery device in accordance with the invention.

FIG. 1 illustrates a rack or a device 10 in accordance with the invention for the processing and delivery of surgical instruments 12. The device 10 comprises a base 14, a rack top 16 pivotally mounted on the base 14, and a pair of self-locking retaining rods or spindles 18 positioned in the base 14 and rack top 16.

Although various fabricating materials may be used for the device 10, a durable, generally rigid polymeric material capable of withstanding ethylene oxide or steam sterilization temperatures is preferred. Polyetherimide, polypropylene and polyphyneloxide are such preferred materials. Polyetherimide is particularly preferred because of its ability to retain its physical properties over long terms from exposure to high temperature steam. Plastics like these are preferable over metals because the plastics are less likely to scratch or otherwise damage instruments supported in the device and because they are non-corroding and generally lighter and less expensive.

Figure 2:
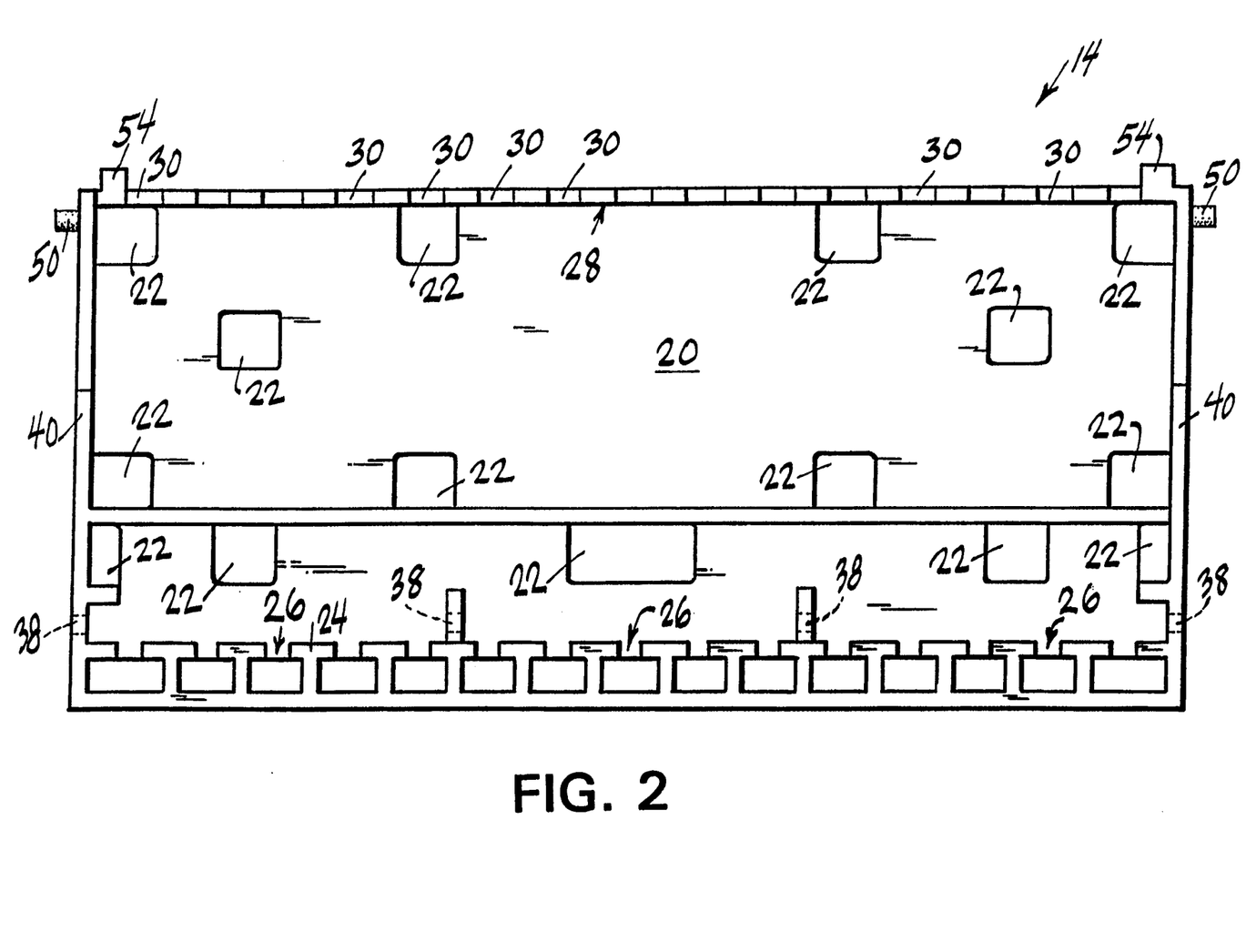
FIG. 2 is a top view of the base portion of the device of FIG. 1.
Figure 3:
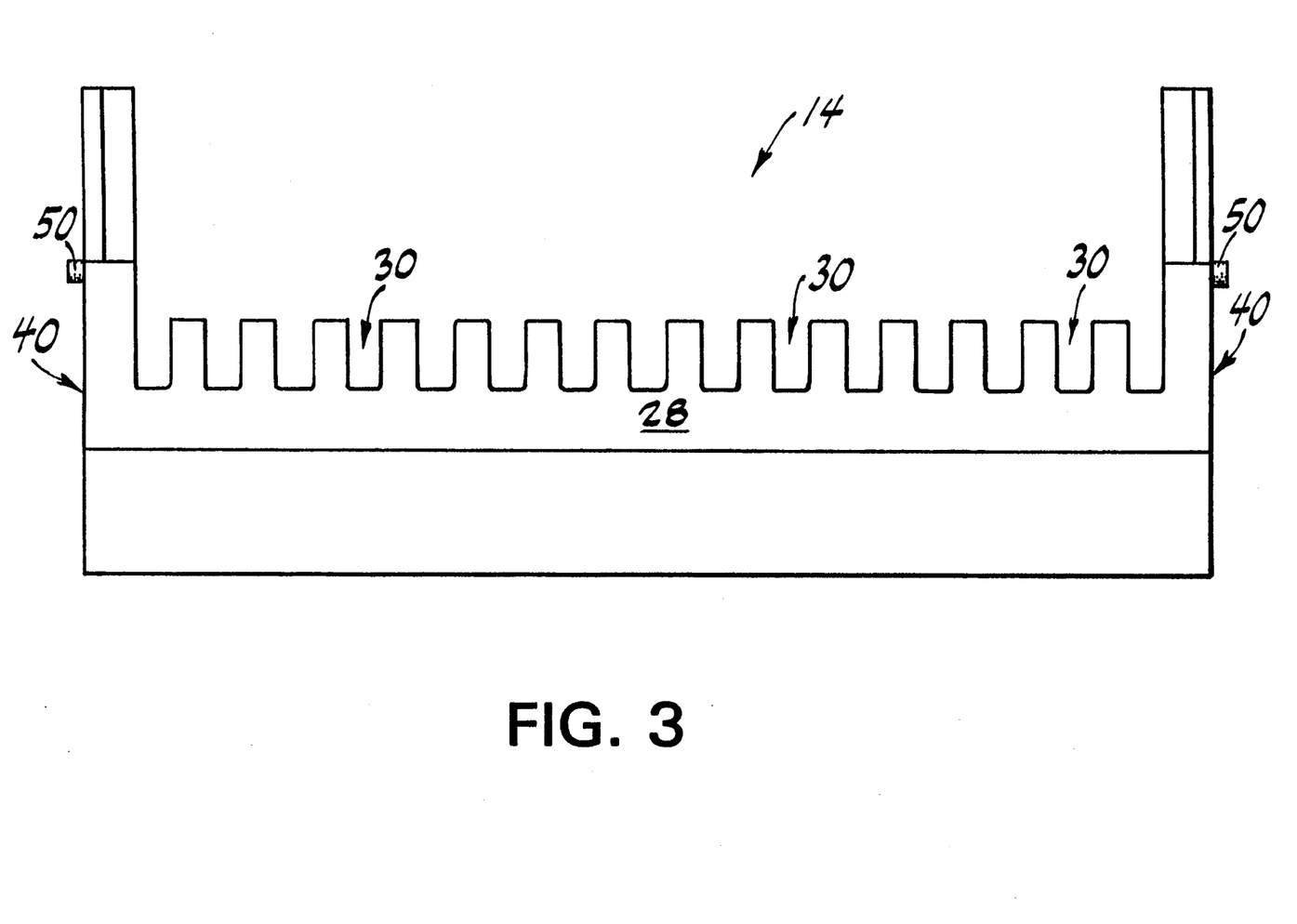
FIG. 3 is a front view of the base shown in FIG. 2.

FIGS. 2 and 3 illustrate top and front views, respectively, of the base 14 without attachment thereto of the rack top 16 or spindle 18. The base 14 has an injected molded single unit construction and is generally rectangular in the top view. The base 14 includes a base bottom 20 having a smooth, flat upper surface. The base bottom 20 includes fifteen strategically located drainage ports 22 for increasing circulation of steam and other sterilizing gases and allowing fluid flow therethrough in automatic washer-sterilizers. In addition, the ports 22 reduce the risk of gross particulate matter being trapped in the device 10.

The base 14 also includes a front portion comprising a front panel 24 having a plurality of spaced-apart slots 26 formed therein. The slots 26 have a width of 3/16" and a height of 1" and are positioned across the length of the front panel 24. The base 14 also includes a rear portion comprising a rear panel 28 opposite the front panel 24 that has a greater height than the front panel 24. The rear panel 28 also includes a plurality of slots 30 therein, each having a 9/32" width and a 9/16" height. Each of the slots 26 in the front panel 24 corresponds with one of the slots 30 in the rear panel 28 such that pairs of corresponding slots are provided for receiving and supporting surgical instruments 12 like that shown in FIG. 1. When ring handled surgical instruments are properly positioned in the front and rear panels 24, 28 each instrument 12 extends along a generally vertical plane with one of its ring handles 32 and lever portions 34 resting in respective slots 26, 30 in the front and rear panels 24, 28 of the base 14. The instruments 12 are arranged in a parallel manner in the base 14 and are prevented from coming into contact with each other and thereby possibly becoming damaged. The distance between the front and rear panels 24, 28 is greater than 4". Because this distance is relatively large in comparison with the width of the slots 26, 30, misalignment of the instruments 12 is inhibited without application of excessive force upon the instruments.

The rear panel 28 has a greater height than the front panel 24 so that the instruments 12 can be supported on the base 14 angulated upward from the ring handles 32 to the working members 36.

When instruments placed in the rack are in a closed position, they are sufficiently spaced apart to allow easy retrieval by operating room staff for delivery to the surgeon. When the instruments are in an open position, the upward angulation of the instruments is sufficient to prevent contact with the mayo stand, back table, or other article on which the rack has been placed.

Positioned along the interior of the front panel 24 of the base 14 are four spaced-apart spindle receiving apertures 38. These apertures 38 are aligned and adapted to receive one of the self-locking retaining spindles 18. The apertures 38 are positioned along the front panel 24 such that when the spindle 18 is passed through the apertures 38, it is also passed through the bottom ring handles 32 of the surgical instruments 12 in the front panel slots 26 to couple the surgical instruments 12 with the base 14.

Figure 8:
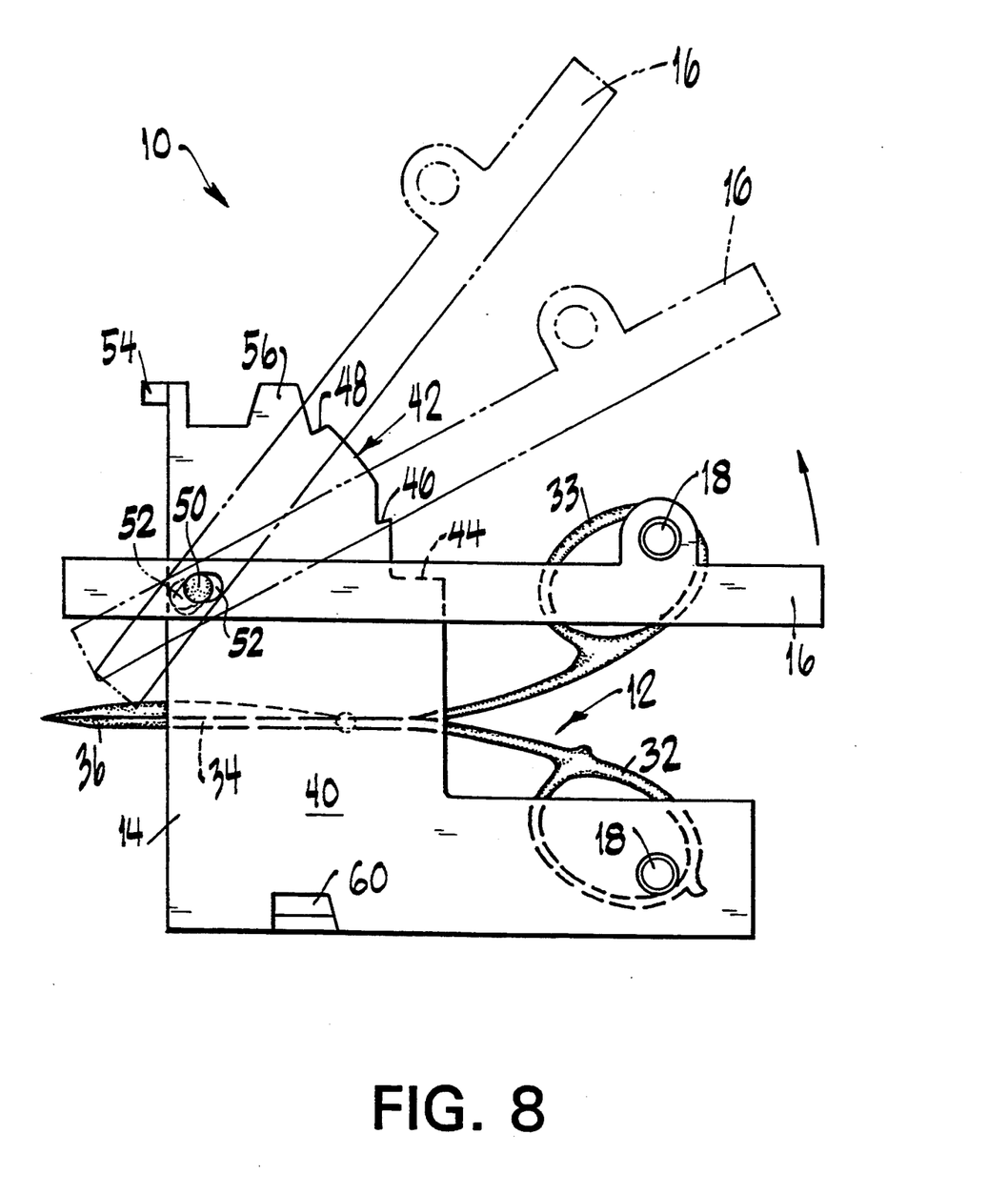
FIG. 8 is a side view of the FIG. 1 device.

The base 14 further comprises a pair opposing of sidewalls 40 extending between the front and rear panels 24, 28. The upper front edge 42 of each sidewall 40 defines a three position cam, which is notched at positions 44, 46, 48 corresponding to 0°, 15° and 30° angles, respectively (see FIG. 8). When the base 14 and the rack top 16 are assembled, the three-position cam allows the top 16 to be oriented at a 0°, 15°, or 30° angles with respect to the base 14 as shown in FIG. 8.

A 3/16" diameter peg 50 extends from the outer sides of each of the sidewalls 40. The pegs 50 are designed to mate with corresponding elongated peg receiving apertures 52 in the rack top 16 (see FIG. 6).

Figure 4:
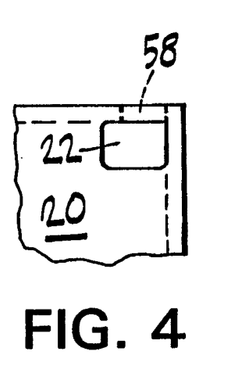
FIG. 4 is a bottom view of a portion of the base floor of the FIG. 1 device illustrating openings therein for facilitating stacking of a plurality of like devices.
Figure 5:
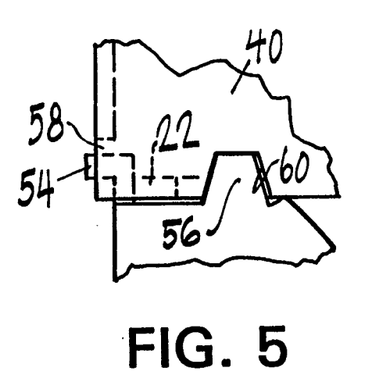
FIG. 5 is a partial side view of two stacked devices.

A 3/16" tab 54 extends upwardly from both the ends of the rear panel 28 and a 5/16" extension 56 projects upwardly from both sidewalls 40 proximate the tabs 54. The drainage ports 22 at the rear corners of the base bottom 20 and openings 58 at the lower corners of the rear panel 28 are adapted to receive the tabs 54 of another device (see FIGS. 4 and 5). Also, slots 60 are formed in each sidewall 40 for receiving the extensions 56 of another device as shown in FIG. 5. This structure permits secure stacking of multiple devices. The devices may be stacked either when filled with instruments or when empty. This stacking feature allows for more efficient and secure use of storage space when storing empty devices. It also allows instruments to be housed safely without risk of damage to other instrument sets when the racks are filled with instruments.

Figure 6:
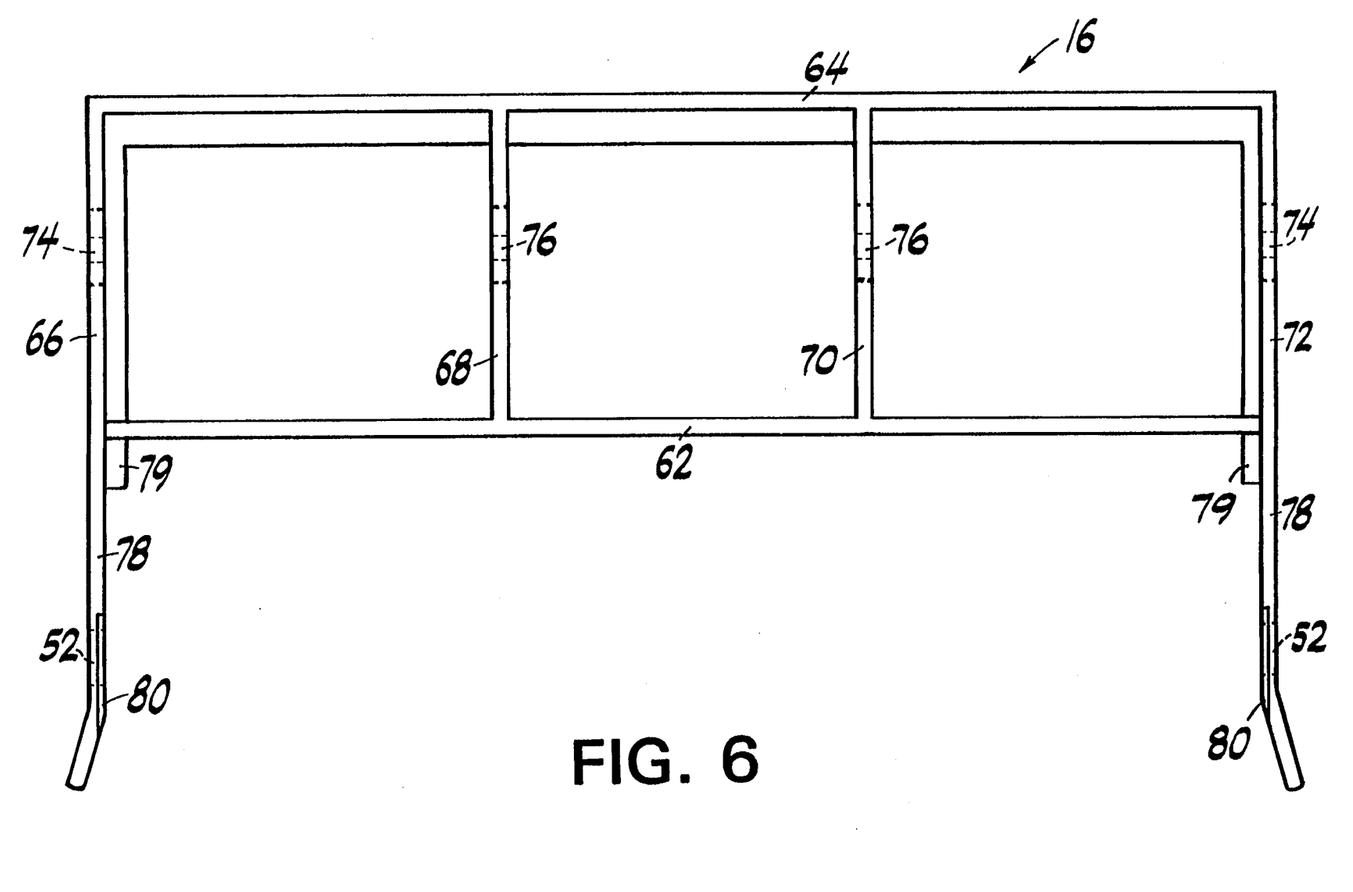
FIG. 6 is a bottom view of the rack top portion of the device of FIG. 1.

As shown in FIG. 6, the rack top 16 comprises a pair of longitudinally extending bars 62, 64 and four members 66, 68, 70, 72, which are connected to and perpendicular to the bars 62, 64. The inner members 68, 70 are each spaced 37/64" inwardly from the outer members 66, 72, respectively. The outer members 66, 72 each have spindle receiving apertures 74 located on the upper sides thereof, and the inner members 68, 70 each have a cavity 76 also on their upper sides. The apertures 74 and cavities 76 are aligned and positioned 13/16" from the outer bar 64. The apertures 74 and cavities 76 are adapted to receive and support one of the self-locking retaining spindles 18 as shown in FIG. 1.

The outer members 66, 72 are each connected with a pair of outwardly extending arms 78. The far end of each arm 78 is flared at a 15° angle and has a guide ledge 80 therein leading to an elongated aperture 52, which is adapted to mate with one of the 3/16" pegs 50 extending from the sides of the base 14.

About the first 1½" of each of the arms 78 extending from the arm aperture 52 toward the bar 62 is ⅛" thick. The remaining portion of each arm proximate the bar 62 and the outer members 66, 72 (approximately 2¾" long) is 9/32" thick. When the base 14 is to be assembled with the rack top 16, the pegs 50 extending from the sides of the base 14 are snapped into the apertures 52. The rack top 16 is thereby pivotally or rotatably coupled with the base 14. The thinner portion of the arms 78 can move freely relative to the three-position cam on the base 14. The thicker portion of each arm, however, includes a mating portion 79 at the end thereof that can be engaged with any one of the three positions 44, 46, 48 of the cam, enabling the rack top 16 to be maintained at various angular positions relative to the base 14 as shown in FIG. 8. The apertures 52 on the rack top for receiving the pegs 50 are elongated to allow the rack top to be moved radially with respect to the pegs 50. The mating portions 79 of the rack top can thereby be moved into and out of engagement with the three positions 44, 46, 48 of the cam to allow the rack top to be moved to and maintained at any of the three cam positions. Thus, to move the rack top from a first cam position to a second cam position, the rack top is first pulled radially away from the pegs 50 to disengage the mating portions 79 from the first cam position. The rack top is then pivoted to the desired second cam position and pushed radially toward the pegs 50 to engage the mating portions with the second cam position.

Figure 7:
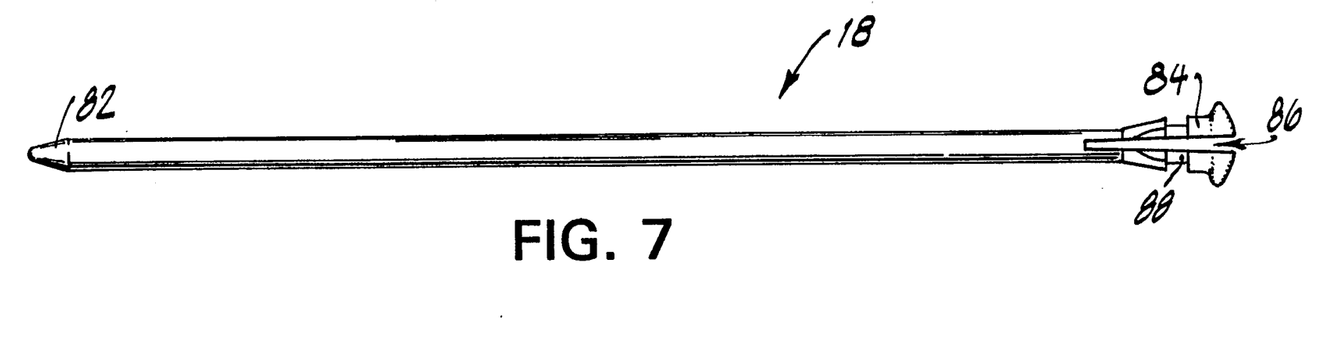
FIG. 7 is side view of one of the spindles of the device of FIG. 1.

The self-locking retaining spindles 18 are designed to pass through and extend slightly beyond the sides of the base 14 and the rack top 16. As shown in FIG. 7 the front tip 82 of each spindle 18 has a 15° taper to facilitate insertion into the bottom and top spindle receiving apertures and cavities 38, 74, 76. The spindles 18 include a self-locking mechanism to releasably lock the spindles 18 in the spindle receiving apertures 38, 74. The back or handle portion 84 of each spindle is flared and slotted at 86 and includes an annular groove 88. The slot 86 allows the handle portion 84 to be compressed, enabling entry of the annular groove 88 into the outer spindle receiving apertures 38, 74 of the base 14 and top 16. Once released, the handle 84 expands to its original size, allowing the annular groove 88 to fit snugly into the spindle receiving aperture, thereby locking the spindle 18 in place.

Ring handled instruments 12 may be loaded in the device 10 as follows. First, the ring-handled end of each instrument 12 and the opposite working end 36 are placed in corresponding front and rear panel slots 26, 30, respectively. Next, one of the spindles 18 is inserted through the spindle receiving apertures 38 in the base 14 and also through one of the ring handles 32 of each instrument 12 to couple the instruments 12 with the base 14. Then, the rack top 16 is pivotally coupled with the base 14. The other spindle 18 is then inserted in the spindle receiving apertures and cavities 74, 76 in the rack top 16 and through the remaining ring handles 33 of the instruments 12 to couple the instruments with the rack top 16. By means of the three-position cam on the base 14, the rack top 16 can be pivoted to 0°, 15°, and 30° angles with respect to the base 14 as shown in FIG. 8. By rotating the rack top 16, the instruments positioned in the device 10 can thus be moved between open and closed positions to facilitate the processing and delivery of the instruments.

Removable tabs (not shown) may be inserted into the slots 30 in the rear panel 28 of the base 14 not occupied by instruments. The tabs are used to indicate that instruments have been deliberately left out of certain slots. This enables a user to quickly and easily confirm the proper count of instruments.

A customized brush (not shown) designed specifically to clean the instruments while still contained in the device 10 opened at a 30° angle is also provided.

The present invention has been described in the foregoing specification with respect to specific embodiments, which serve as examples to illustrate the invention rather than to limit its scope. Modification may be made to the described embodiments without departing from the broad teachings of the invention.

We claim:

1. A rack for the processing and delivery of ring-handled surgical instruments, each of the instruments having first and second ring handles at one end thereof connected with lever members to an opposite end, said rack comprising:

two spindles;

a base having opposing front and rear panels, said front and rear panels each including a plurality of slots therein for supporting said instruments wherein each slot in said front panel corresponds to one of said slots in said rear panel such that said one end of each of said surgical instruments may be positioned in a slot in said front panel and said opposite end may be positioned in the corresponding slot in said rear panel, said base also including a plurality of apertures proximate said front panel wherein one of said spindles extends through said aperture and is extendable through the first ring handles of said surgical instruments to couple the instruments with said base; and a rack top including a plurality of apertures wherein the other of said spindles extends through said apertures of the rack top and is extendable through said second ring handles of said surgical instruments to couple the instruments with the rack top, said rack top being pivotally connected with said base proximate said rear panel so that surgical instruments coupled with the base and rack top may be moved between open and closed positions by pivoting said rack top relative to said base.

2. The rack of claim 1, wherein said base and said rack top each include two apertures through which one of said spindles extends.

3. The rack of claim 1, wherein said base, said spindles and said rack top comprise polymeric material.

4. The rack of claim 1, wherein said base, said spindles and said rack top comprise polyetherimide.

5. The rack of claim 1, wherein said base, said spindles and said rack top comprise polyphyneloxide or polypropylene.

6. The rack of claim 1, wherein said base further comprises a variable position mechanism for enabling the rack top to be maintained at various angular positions relative to said base.

7. The rack of claim 6, wherein said base further comprises a pair of opposing sidewalls between said front and rear panels, and wherein said variable position mechanism comprises a three-position cam formed on surfaces of said sidewalls.

8. The rack of claim 7, wherein said three position cam includes means for enabling the rack top to be maintained at orientations of approximately 0°, 15°, and 30° with respect to said base.

9. The rack of claim 1, wherein said base includes a base bottom and at least one drainage port therethrough.

10. The rack of claim 1, wherein said base further comprises at least one opening and one extension to enable said rack to be securely stacked.

11. The rack of claim 1, wherein said base includes a pair of pegs extending therefrom and said rack top includes a pair of peg receiving apertures to mate with said pegs for pivotally connecting said rack top to said base.

12. The rack of claim 11, wherein said rack top includes a pair of arms extending from opposite ends thereof and wherein each of said peg receiving apertures extends through one of said arms.

13. The rack of claim 12, wherein each of said arms includes a flared end with a guide ledge therein leading to one of said peg receiving apertures to facilitate mating with said pegs.

14. The rack of claim 1, wherein said spindles each include a locking mechanism for releasably locking said spindles in one of said apertures for receiving said spindles.

15. The rack of claim 14, wherein said locking mechanism comprises a compressible handle and an annular groove.

16. The rack of claim 1, further comprising removable tabs adapted for placing in and marking slots not occupied by instruments.

17. The rack of claim 1, wherein said slots in said rear panel have an approximate width of 9/32 and said slots in said front panel have an approximate width of 3/16.

18. The rack of claim 1, wherein the front and rear panels are spaced apart a distance of at least 4 inch.

19. The rack of claim 1, wherein said rear panel has a greater height than said front panel.

20. The rack of claim 1, wherein said base and rack top comprise injection molded parts.

21. A device for the cleansing, storage and presentation of ring-handled surgical instruments, each of the instruments having two ring handles at one end thereof connected by lever members to working members at an opposite end, said device comprising:

two rods;

a base having opposing front and rear portions, said front and rear portions each including a plurality of slots therein for supporting said instruments wherein each slot in said front portion corresponds to one of said slots in said rear portion such that said one end of each of said surgical instruments may be positioned in a slot in said front portion and said opposite end may be positioned in a corresponding slot in said rear portion, said base also including a plurality of apertures in said front portion wherein one of said rods extends through said apertures and is extendable through one of the ring handles of each surgical instrument to couple the instruments with said base; and a rack top including a plurality of apertures being positioned in said rack top such that the other of said rods extends through said apertures of the rack top and is extendable through the other of said ring handles of each surgical instrument to couple the instruments with the rack top, said rack top being pivotally connected with said base proximate said rear portion such that surgical instruments coupled with the base and the rack top may be moved between open and closed positions by pivoting said rack top relative to said base.

22. The device of claim 21, wherein said base, said rods, and said rack top comprise polymeric material.

23. The device of claim 21, wherein said base, said rods, and said rack top comprise polyetherimide.

24. The device of claim 21, wherein said base, said rods, and said rack top comprise one of polyphyneloxide and polypropylene.

25. The device of claim 21, wherein said base further comprises a variable position mechanism for enabling the rack top to be maintained at various angular positions relative to said base.

26. The device of claim 25, wherein said base further comprises a pair of opposing sidewalls between said front and rear portions, and wherein said variable position mechanism comprises a three-position cam formed on surfaces of said sidewalls.

27. The device of claim 26, wherein said three position cam includes means for enabling the rack top to be maintained at orientations of approximately 0°, 15°, and 30° with respect to said base.

28. The device of claim 21, wherein said base includes a base bottom and at least one drainage port therethrough.

29. The device of claim 21, wherein said base further comprises an opening and an extension to enable secure stacking of said device.

30. The device of claim 21, wherein said base includes a pair of pegs extending therefrom and said rack top includes a pair of peg receiving apertures to mate with said pegs for pivotally connecting said rack top to said base.

31. The device of claim 30, wherein said rack top includes a pair of arms extending from opposite ends thereof and wherein each of said peg receiving apertures extends through one of said arms.

32. The device of claim 31, wherein each of said arms includes a flared end with a guide ledge therein leading to one of said peg receiving apertures to facilitate mating with said pegs.

33. The device of claim 21, wherein said rods each include a locking mechanism for releasably locking said rods in said apertures for receiving said rods.

34. The device of claim 33, wherein said locking mechanism comprises an compressible handle and an annular groove.

35. The device of claim 21, further comprising removable tabs adapted for placing in and marking slots not occupied by instruments.

36. A device for the processing and delivery of ring-handled surgical instruments, each of the instruments having first and second ring handles at one end thereof connected with lever members to an opposite end, said device comprising:
 a base having opposing front and rear portions including means for supporting both ends of each of the instruments such that the instruments are generally parallel, vertically oriented, and spaced-apart;
 means for coupling the front portion of the base with the first ring handle of each instrument;
 a rack top pivotally connected with said base at said rear portion; and
 means for coupling the rack top with the second ring handle of each instrument such that surgical instruments coupled with the base and the rack top may be moved between open and closed positions by pivoting said rack top relative to said base.

37. The device of claim 36, wherein said base and said rack top comprise polymeric material.

38. The device of claim 36, wherein said base and said rack top comprise polyetherimide.

39. The device of claim 36, wherein said base and said rack top comprises one of polyphyneloxide and polypropylene.

40. The device of claim 36, further comprising means for positioning said rack top at various angular positions relative to said base.

41. The device of claim 40, wherein said base further comprises a pair of opposing sidewalls between said front and rear portions, and wherein said means for positioning said rack top comprises a variable position cam formed on surfaces of said sidewalls.

42. The device of claim 36, wherein said base includes a base bottom and at least one drainage port therethrough.

43. The device of claim 36, wherein said base further comprises an opening and an extension to enable said device to be securely stacked.

* * * * *